United States Patent
Stock et al.

(10) Patent No.: US 10,227,755 B2
(45) Date of Patent: Mar. 12, 2019

(54) SYSTEMS AND METHODS FOR MONITORING WEAR OF REDUCING ELEMENTS

(71) Applicant: VERMEER MANUFACTURING COMPANY, Pella, IA (US)

(72) Inventors: Joseph D. Stock, Newton, IA (US); Ty Hartwick, Pella, IA (US)

(73) Assignee: Vermeer Manufacturing Company, Pella, IA (US)

( * ) Notice: Subject to any disclaimer, the term of this patent is extended or adjusted under 35 U.S.C. 154(b) by 209 days.

(21) Appl. No.: 15/120,401

(22) PCT Filed: Feb. 18, 2015

(86) PCT No.: PCT/US2015/016350
§ 371 (c)(1),
(2) Date: Aug. 19, 2016

(87) PCT Pub. No.: WO2015/126923
PCT Pub. Date: Aug. 27, 2015

(65) Prior Publication Data
US 2017/0067229 A1    Mar. 9, 2017

Related U.S. Application Data

(60) Provisional application No. 61/941,828, filed on Feb. 19, 2014.

(51) Int. Cl.
*E02F 9/26* (2006.01)
*E02F 5/08* (2006.01)
(Continued)

(52) U.S. Cl.
CPC .............. *E02F 9/267* (2013.01); *B60R 1/002* (2013.01); *E02F 5/08* (2013.01); *E02F 9/2054* (2013.01);
(Continued)

(58) Field of Classification Search
CPC ......... E02F 9/267; E02F 9/2054; E02F 9/268; E02F 9/2866; E02F 5/08; B60R 1/002;
(Continued)

(56) References Cited

U.S. PATENT DOCUMENTS 6,369,376 B1   4/2002  Gerlach
6,990,390 B2   1/2006  Groth et al.
(Continued)

FOREIGN PATENT DOCUMENTS

AT       382 683       3/1987
AU    2009212871 B2    3/2010
(Continued)

OTHER PUBLICATIONS

Extended European Search Report for corresponding European Patent Application No. 15752480.2 dated Jan. 11, 2018, 11 pages.
(Continued)

*Primary Examiner* — Abby Y Lin
(74) *Attorney, Agent, or Firm* — Merchant & Gould P.C.

(57) ABSTRACT

Aspects of the present disclosure relate to display structures for displaying the wear status of reducing elements (e.g., chisels, teeth, etc.) on a reducing component. In certain examples, the display structure can include a matrix that visually depicts all of the reducing elements of the reducing component in a row and column format. The wear status of the reducing elements can be indicated by techniques such as different colors, different numbers, different letters, shapes, bar codes etc. Another aspect of the present disclosure relates to an autonomous system where a remote party can simultaneously monitor the wear status of the reducing elements of multiple machines on the display structure. For each machine, the remote party (e.g., operator, supply source, supervisor, and main office) can each receive a
(Continued)

wireless signal indicating when the reducing elements are approaching a need for replacement.

17 Claims, 10 Drawing Sheets

(51) Int. Cl.
    *B60R 1/00*     (2006.01)
    *E21C 25/10*     (2006.01)
    *E02F 9/20*     (2006.01)
    *E02F 9/28*     (2006.01)
    *G09G 5/34*     (2006.01)
    *G01N 3/56*     (2006.01)

(52) U.S. Cl.
    CPC ............ *E02F 9/268* (2013.01); *E02F 9/2866* (2013.01); *E21C 25/10* (2013.01); *B60R 2300/802* (2013.01); *G01N 3/56* (2013.01); *G09G 5/34* (2013.01); *G09G 2380/10* (2013.01)

(58) Field of Classification Search
    CPC ..... B60R 2300/802; E21C 25/10; G01N 3/56; G09G 5/34; G09G 2380/10
    See application file for complete search history.

(56) References Cited

U.S. PATENT DOCUMENTS

| | | | |
|---|---|---|---|
| 7,290,360 B2 | 11/2007 | Unzicker et al. | |
| 7,406,399 B2* | 7/2008 | Furem | E02F 9/267 |
| | | | 37/379 |
| 7,689,394 B2* | 3/2010 | Furem | E02F 9/2054 |
| | | | 703/8 |
| 7,979,181 B2 | 7/2011 | Clark et al. | |
| 8,386,196 B2* | 2/2013 | Wagner | B28D 7/00 |
| | | | 175/39 |
| 8,775,099 B2 | 7/2014 | Wagner et al. | |
| 9,863,247 B2* | 1/2018 | Von der Lippe | E21C 35/00 |
| 2005/0085973 A1 | 4/2005 | Furem et al. | |
| 2010/0076697 A1 | 3/2010 | Wagner et al. | |
| 2013/0032634 A1* | 2/2013 | McKirdy | A61B 5/0205 |
| | | | 235/375 |
| 2013/0049935 A1 | 2/2013 | Miller et al. | |
| 2013/0128279 A1* | 5/2013 | Wachsmann | E01C 23/01 |
| | | | 356/601 |
| 2014/0007465 A1 | 1/2014 | Cutler et al. | |
| 2015/0322634 A1 | 11/2015 | Stock et al. | |

FOREIGN PATENT DOCUMENTS

| | | |
|---|---|---|
| DE | 44 15 824 C1 | 11/1995 |
| DE | 100 15 005 A1 | 10/2001 |
| EP | 1 447 481 A1 | 8/2004 |
| SU | 1159991 A1 | 7/1985 |
| WO | 2014/093625 A1 | 6/2014 |

OTHER PUBLICATIONS

International Search Report for corresponding International Patent Application No. PCT/US2015/016350 dated Jun. 3, 2015, 3 pgs.
Partial Supplementary European Search Report for corresonding European Patent Application No. 15752480.2 dated Sep. 27, 2017, 13 pages.
Russian Office Action and Search Report for corresponding Russian Patent Application No. 2016134945 dated Sep. 13, 2018, 11 pages.

* cited by examiner

SYSTEMS AND METHODS FOR MONITORING WEAR OF REDUCING ELEMENTS

This application is a National Stage Application of PCT/US2015/016350, filed Feb. 18, 2015, which claims priority to U.S. Provisional Patent Application No. 61/941,828, filed Feb. 19, 2014, the disclosure of which is hereby incorporated by reference herein in its entirety. To the extent appropriate, a claim of priority is made to each of the above disclosed applications.

TECHNICAL FIELD

The present disclosure relates generally to systems and methods for sensing wear in an autonomous system of machines designed to reduce or break-down material. In an autonomous system a remote party can monitor one or more machines working in tandem and/or independent of each other. More particularly, the present disclosure relates to systems and methods for sensing wear of reducing elements used by excavation machines such as surface excavation machines.

BACKGROUND

Relatively hard materials are often processed for mining and construction. The variety of materials include rock, concrete, asphalt, coal and a variety of other types of mineral-based material. A number of different methods for reducing the size of these hard materials have been developed. One traditional material size reduction method has been to drill relatively small holes in the material which are then packed with an explosive that is ignited, resulting in a rapid and cost effective method of size reduction. However, there are a variety of disadvantages to this technique including the inherent risk of injuries, the production of undesirable noise, vibrations, and dust, and the fact that this process is difficult to utilize in situations where space is limited or where there is a potential risk of causing other gases to ignite.

Due to the above-described disadvantages associated with blasting techniques, alternative methods have been developed for reducing relatively hard materials. The main alternative has been the use of reducing machines having rotary reducing components that move rigid and specialized reducing elements through paths of travel. The reducing components can include rotating drums that move the reducing elements through circular paths of travel. Such drums are typically attached to their corresponding machines so that the positions and orientations of the drum can be controlled to bring the reducing elements into contact with the material being reduced. Alternative reducing components can include boom-mounted chains that carry reducing elements. The chains are typically driven/rotated about their corresponding booms. The reducing elements are mounted to and move along the paths of travel defined by the chains. In use, the booms are moved (e. g., through a pivoting motion) to positions where the reducing elements are brought into contact with the material being reduced.

An example machine of the type described above is disclosed at U.S. Pat. No. 7,290,360. The disclosed machine is a surface excavation machine used for applications such as surface mining, demolishing roads, terrain leveling, and prepping sites for new construction or reconstruction by removing one or more layers of material. Surface excavation machines of this type provide an economical alternative to blasting and hammering and provide the advantage of generating a consistent output material after a single pass. This can reduce the need for primary crushers, large loaders, large haul trucks and the associated permits to transport materials to crushers.

The reducing elements of reducing machines have been developed to withstand the impact loads and abrasion associated with material reduction activities. Reducing elements can be constructed in a variety of shapes and sizes and have been labeled with various terms including cutters, chisels, picks, teeth etc. Typical reducing elements include leading impact points or edges and bases. The bases are constructed to fit into mounting structures that are integrated with drums or chains used to carry the reducing elements during material reducing applications. The harsh environment associated with material reducing applications virtually guarantees that the reducing elements will wear down over time. Thus, the reducing elements are designed to be replaceable, while the mounting structures are not intended to be replaced frequently. For example, when a given reducing element becomes worn, it is removed from its corresponding mounting structure and replaced with a new, unworn reducing element.

Often, the tips or edges of the reducing elements have a harder construction (e.g., a solid carbide construction) than the bases of the reducing elements. When using new reducing elements to reduce material, the leading points or edges are exposed to the majority of the impacts and abrasion action. However, once the leading tips or edges becomes worn, the bases are exposed to more impacts and abrasive action. A variety of potential problems can arise when this occurs, including that the bases are less efficient at breaking the material, causing inefficient operation. This inefficiency may result in generation of sparks and/or excessive heat, which could lead to a risk of explosions and/or fires, as may occur in a coal mining application where methane gas can be present. Additionally, the bases will typically wear relatively quickly as compared to the leading points or tips. This is significant because the bases prevent the reducing element mounting structures from being exposed to wear. Thus, once the leading edges or points of the reducing elements are worn away, the machines can only be operated for a relatively short period of time before the bases wear away, resulting in a situation where the mounting structures of the drums or chains are contacting the material being reduced. Once a reducing elements are worn to this point, there is a risk of causing damage to the mounting structures of the drums or chains. The mounting structures are not intended to be repaired easily, so the resulting potential damage can be difficult and costly to repair.

As a result of these issues, there are significant benefits to replacing reducing elements before the wear has progressed to an unacceptable point. Systems have been designed to monitor the condition of cutters to allow operators to interrupt operation and replace cutters at appropriate times. Example systems for monitoring reducing element wear are disclosed in AT3826832; DE 10015005; and US 2010/0076697. While wear sensing systems exist, improvements are needed in this area.

SUMMARY

Aspects of the present disclosure relate to display structures for displaying the wear status of reducing elements (e.g., chisels, teeth, etc.) on a reducing component. In certain examples, the display structure can include a matrix that visually depicts all of the reducing elements at once in real time. The wear status of the reducing elements can be indicated by techniques such as providing different colors, different numbers, different letters, bar codes, shapes, etc., equating to a particular level of wear. In one example, a color coded system can be used in which green indicates a given tooth as an acceptable level of wear, yellow indicates that a given tooth has a medium amount of wear, and red indicates that a given tooth is in need of replacement. In certain examples, a flashing red indicates that a given tooth needs immediate replacement. In such examples, a control system for a machine may automatically stop operation of the machine once a given reducing element reaches a pre-determined wear state.

In one example, an operator can manually select a reducing element, and a controller will automatically index the drum so that the selected reducing element is positioned at a particular index position (change-out position) for accessing and replacing the reducing element. In certain examples, the display structure can include a scrolling matrix, in which the rotational position of the reducing elements relative to a reference point is detected in real time. Alternatively, the controller can be provided with an algorithm or other control logic that automatically indexes an excavation drum to the change-out position upon request by the operator. Such an operation may be performed remotely or on-site.

Another aspect of the present disclosure relates to an autonomous system where a remote party can monitor one or more machines on a display for status wear of the reducing elements. The remote party may include an operator, a supervisor, a main office, warehouse, etc. A wireless signal can be sent to the remote party to alert when the reducing elements are approaching a need for replacement. This system can allow for preordering of parts for the reducing elements and/or for tracking how often the reducing elements are being replaced.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

DETAILED DESCRIPTION

Figure 1:
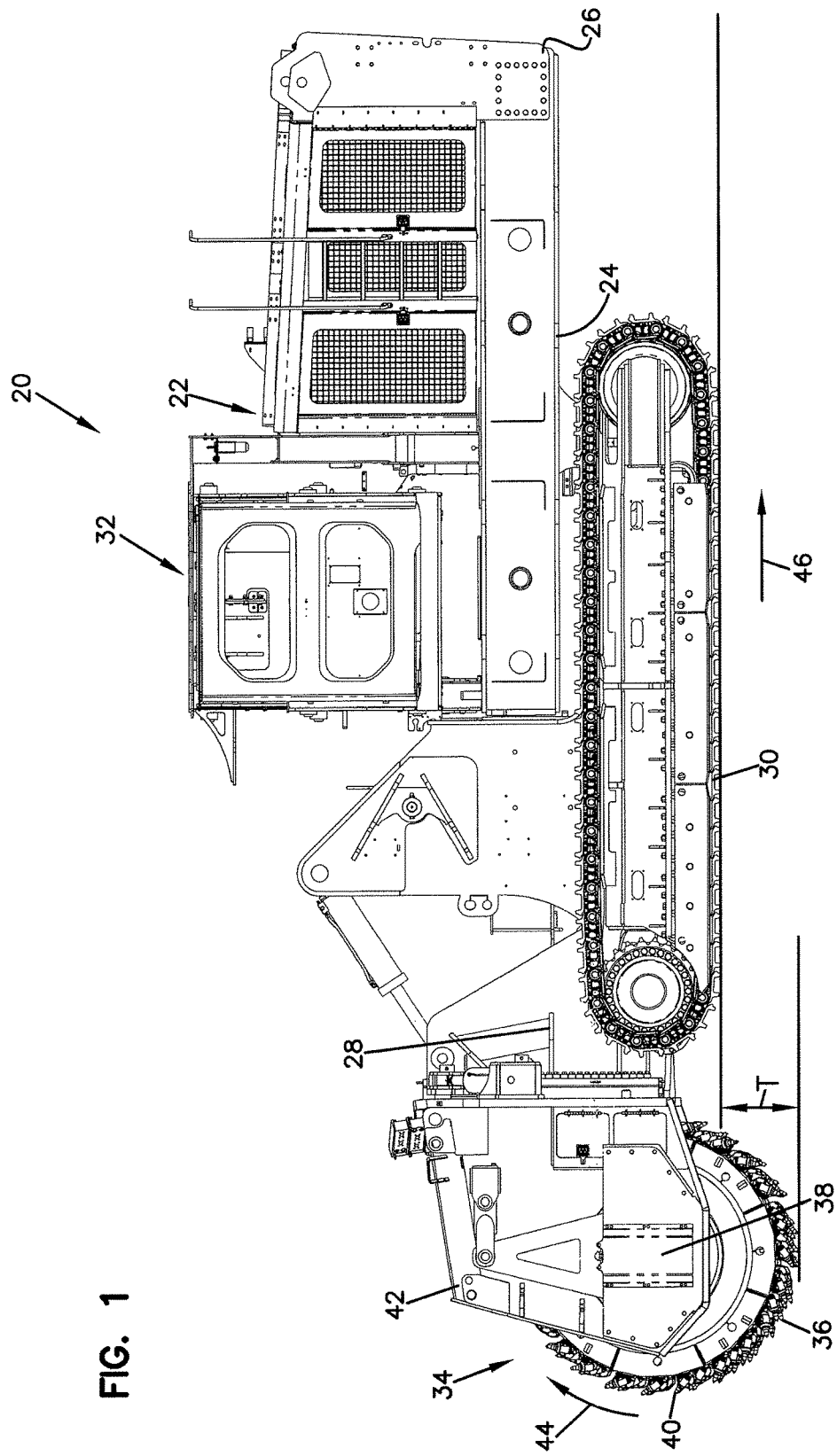
FIG. 1 shows a side view of a surface excavation machine incorporating a reducing element wear sensing system in accordance with the principles of the present disclosure.

FIG. 1 illustrates an example of a surface excavation machine 20 (e.g., autonomous machine) that includes a tractor 22 having a main chassis 24 (i.e., a mainframe) including a front end 26 and a rear end 28. The main chassis 24 is supported on a ground drive system (i.e., a propulsion system) that can include multiple propulsion structures such as wheels or tracks 30 for propelling the surface excavation machine 20 over the ground. An operator cab 32 is positioned at a top side of the main chassis 24. An excavation tool 34 is mounted at the rear end 28 of the main chassis 24. The excavation tool 34 includes an excavation drum 36 that is rotatably driven (e.g., by hydraulic motors) about a drum axis 38. The excavation drum 36 carries multiple reducing elements 40 (e.g., teeth) suitable for cutting rock or another hard, mineral-based material (e.g., asphalt, concrete). The excavation drum 36 can be mounted to a boom that can be pivoted between a lowered excavation position (see FIG. 1) and a raised transport position (not shown). A shroud 42 at least partially surrounds/encloses the excavation drum 36. In other embodiments the excavation drum 36 may not be mounted.

In use of the surface excavation machine 20, the surface excavation machine 20 is moved to an excavation site while the excavation tool 34 is in the transport position. When it is desired to excavate at the excavation site, the excavation tool 34 is lowered from the transport position to the excavation position (see FIG. 1). While in the excavation position, the excavation drum 36 is rotated in a direction 44 about the axis 38 such that the excavation drum 36 uses an up-cut motion to remove a desired thickness T of material. During the excavation process, the tracks 30 propel the surface excavation machine 20 in the forward direction 46, thereby causing a top layer of material having a thickness T to be excavated. As the surface excavation machine 20 moves in a forward direction 46, the reducing elements 40 dig into the material under the excavation drum 36, leaving behind excavated material. Example excavation applications for which the surface excavation machine 20 can be used include surface mining, road milling, terrain leveling, construction preparation and other activities. In other examples, the drum 36 can be configured to excavate using either an up-cut motion or a down-cut motion.

Figure 2:
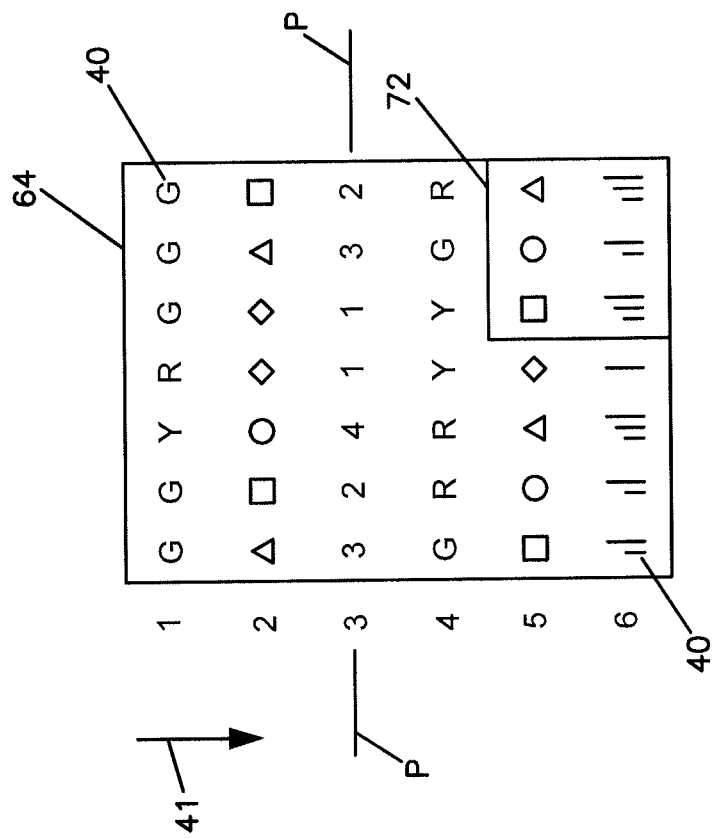
FIG. 2 illustrates an example of a display monitor in a scrolling matrix having a row and column format.
Figure 3:
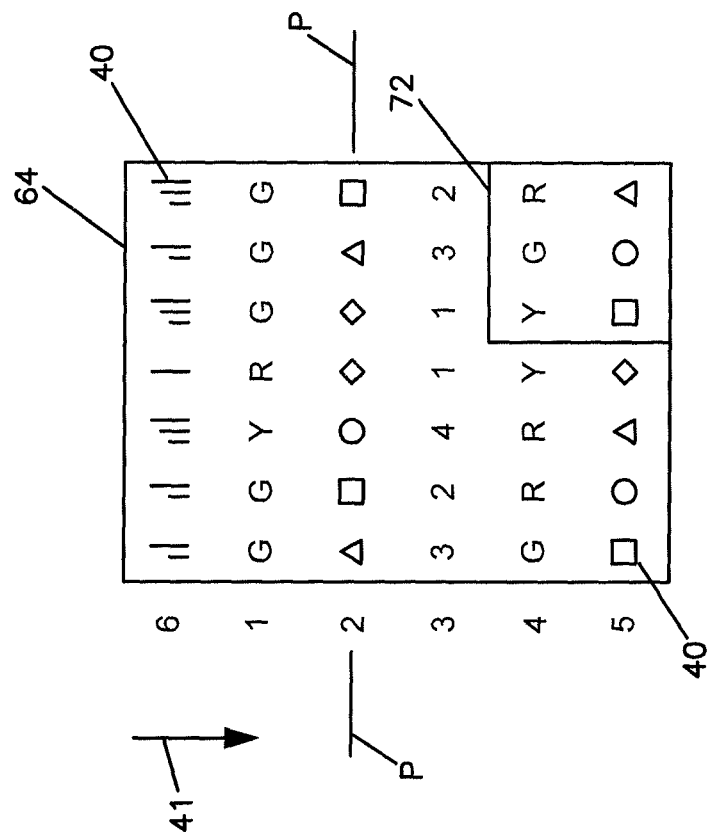
FIG. 3 is the display monitor showing the features of the scrolling matrix depicted in FIG. 2.
Figure 4:
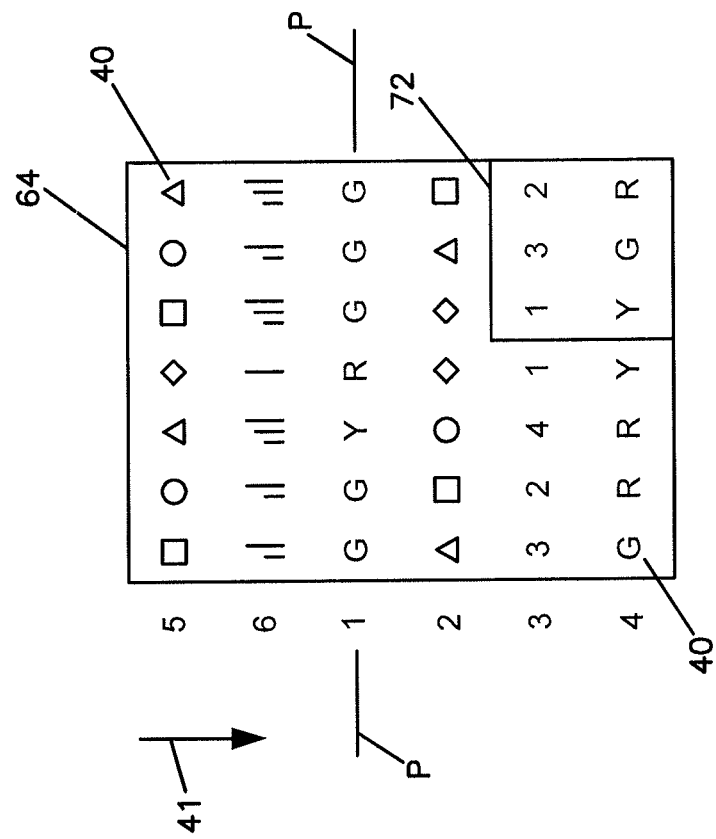
FIG. 4 is the display monitor showing the features of the scrolling matrix depicted in FIG. 2.
Figure 5:
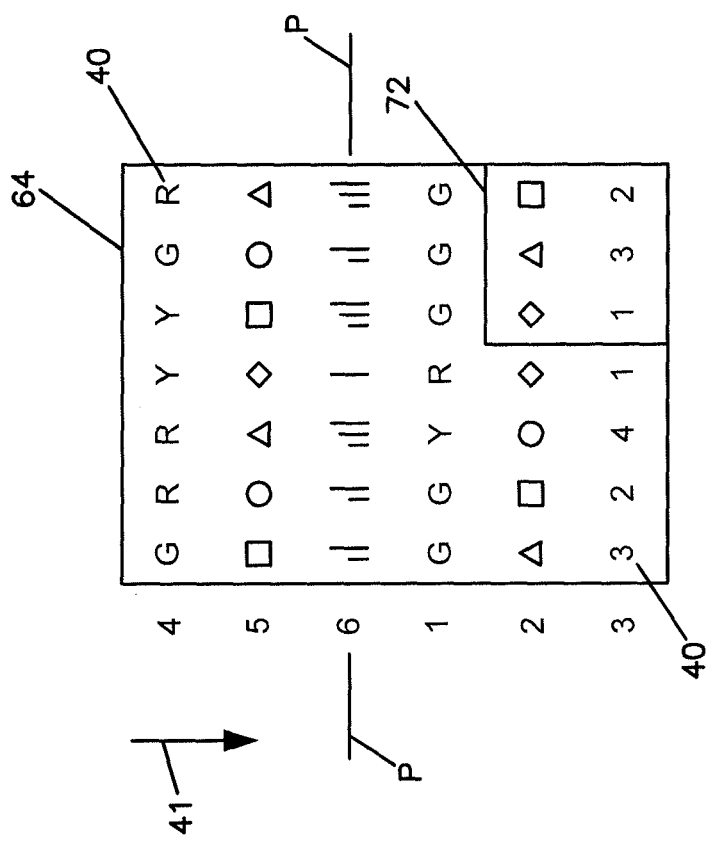
FIG. 5 is the display monitor showing the features of the scrolling matrix depicted in FIG. 2.
Figure 6:
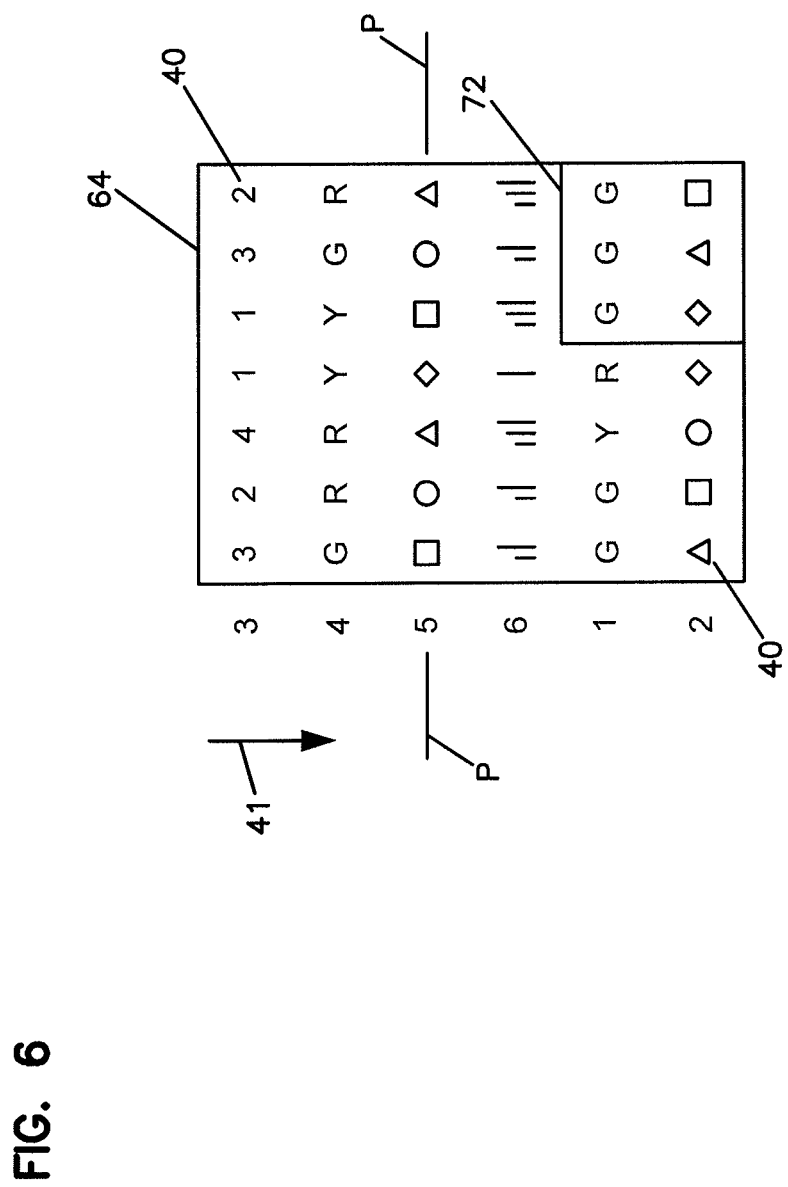
FIG. 6 is the display monitor showing the features of the scrolling matrix depicted in FIG. 2.
Figure 7:
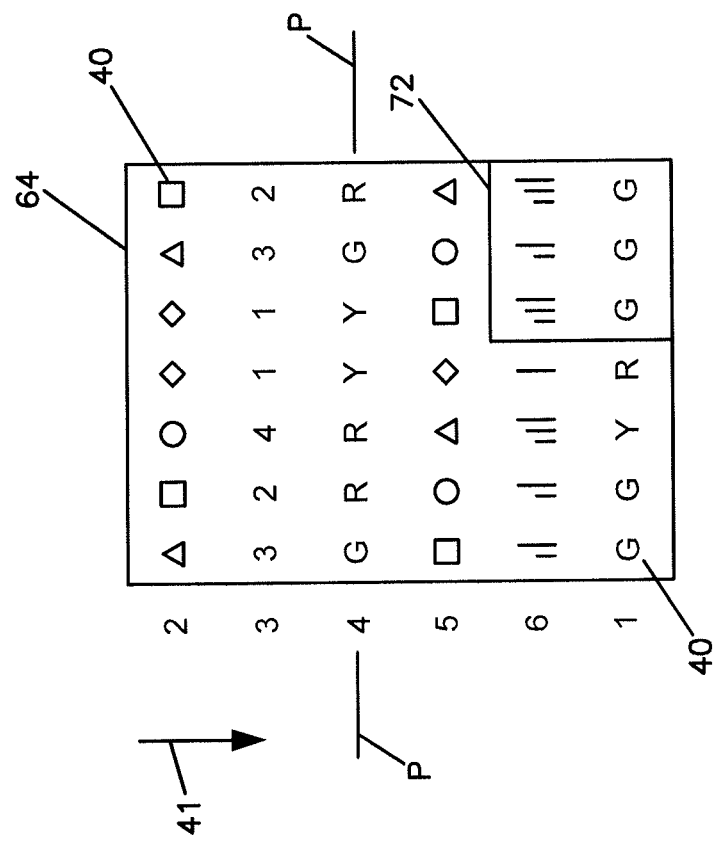
FIG. 7 is the display monitor showing the features of the scrolling matrix depicted in FIG. 2.

Referring to FIG. 2, an example of a display monitor 64 depicting the reducing elements 40 in a scrolling matrix having a row and column format is shown. In the example depicted the display monitor 64 displays 6 rows and 7 columns of reducing elements 40. It will be appreciated that the number of rows and columns may vary with other embodiments. In certain examples, the display monitor 64 can be mounted in a cabin of the surface excavation machine 20 or the display monitor 64 can be a mobile unit that may be used remotely. Example reducing elements 40 are illustrated and described in more detail in FIG. 10.

In one example, the rows of reducing elements 40 scroll in a direction 41 along the matrix screen as the excavation drum 36 rotates to provide a visual indication of the circumferential positions of the reducing elements 40 at a given point in time (e.g., in real time). In other words, the display monitor 64 can be configured to visually scroll through the rotational position of the reducing elements 40 to allow the wear of the reducing elements 40 to be visually monitored in real time. For example, FIGS. 2-7 show the scrolling rotational positions of the reducing elements 40 displayed on the display monitor 64. In certain examples, the display monitor 64 can be used to visually see/represent all of the reducing elements 40 together at once in real time. The display monitor 64 can display the wear status of the reducing elements 40 all at once such that an operator can visually see the wear status of each of the reducing elements 40 being displayed.

The wear status of the reducing elements 40 can be indicated by techniques such as color codes, number codes, letter codes, bar codes, graphs, shapes, etc. If the reducing elements 40 have hit a warning threshold or are in need of replacing, the display monitor 64 will indicate such conditions by using, for example, a code. In one example, a color coded system can be used in which green indicates a given reducing element 40 has an acceptable level of wear, yellow indicates that a given reducing element 40 has a medium amount of wear, and red indicates that a given reducing element 40 is in need of replacement. Alternatively or in combination, an audible warning (e.g., buzzer, recorded message) and/or other sensible warning (e.g., a flashing light) could also be employed as part of the system.

Referring to FIGS. 2-7, the display monitor 64 includes various codes for displaying the wear of the reducing elements 40. In the depicted example, a variety of codes are shown, such as, color codes, number codes, bar codes, and geometry codes. It will be appreciated that other codes may be displayed. In the depicted example, the color codes are indicated by letters G (green), Y (yellow), and R (red). In certain examples, a blinking red light or screen symbol indicates that a given reducing element 40 needs immediate replacement. In other examples, similar levels of wear can be indicated on the display monitor 64 by using different numbers, shapes, and bar codes. The number codes can indicate wear by having a number between 1-10 represent the amount of wear such that the lowest number 1 indicates little to no wear and the highest number 10 indicates great or significant amount of wear (e.g., like the colors above, a blinking "10" on the screen could be used to indicate the need for an immediate replacement). Similarly, the bar codes can indicate the amount of wear by having the number of bars represent the amount of wear on the reducing elements 40, such that one bar indicates little to no wear and three more bars indicate significant amounts of wear. The type of shape can also be used to indicate the amount of wear. A square can be used to represent an acceptable level of wear, a circle can represent a medium amount of wear, a triangle can represent a significant amount of wear, and a diamond can represent a need for replacement.

In certain examples, the display monitor 64 can be configured to show a smaller window 72 for viewing fewer reducing elements 40 in a given area on the excavation drum 36. The display monitor 64 can be arranged and configured to allow the operator to hone in on a specific reducing element 40. In such configuration, the operator can view and diagnose the reducing element 40 closely from the display monitor 64 for wear and determine whether a replacement is needed.

In other examples, the display monitor 64 can be configured to include a change-out position P used as a reference location for changing out the reducing elements 40 once they have hit a warning threshold or are in need of replacement. In some examples, an operator can use a controller to manually index or stop the rotation of the excavation drum 36 to align a given row with the change-out position P while using the display monitor 64 to provide a visual indication of the real time rotational position of the drum 36.

The display monitor 64 can be used to facilitate autonomous operation of an excavation machine. In an autonomous system, the display monitor 64 can be used remotely by someone who may be monitoring multiple machines at once. In other words, autonomous means an operator is remotely monitoring/controlling operation of at least one excavation machine (e.g., at least one surface miner) under certain conditions, multiple excavation machines (e.g., surface miner) can be autonomously monitored/controlled at once. For example, an operator, a supervisor, a third party, and/or any member of the control team may be remotely monitoring multiple machines working in tandem and/or separately. The remote individual(s) may use the display monitor 64 to view operating conditions of each of the multiple machines being controlled. For example, each of the machines within the autonomous system can be monitored remotely by using the display monitor 64 to visually inspect the wear status of the reducing elements 40. In one example, the remote individual(s) may use the display monitor 64 to toggle or move between display screens of multiple machines by pushing a physical button or other toggle, touching or clicking on a screen icon, etc. Each machine can have its own display screen that can be displayed on the display monitor 64 when desired. That is, depending on the viewing setup, one or more display screens could be displayed on the display monitor 64. In other examples, one or more display monitors 64 could be employed, depending, in part, on the number of excavation machines being monitored. By remotely monitoring the machines in the autonomous system, there is the potential for less down time, e.g., resulting from stops to check the wear status of the reducing elements 40. By using the display monitor(s) 64 remotely, all of the autonomous machines can be monitored in real time while in use.

Figure 8:
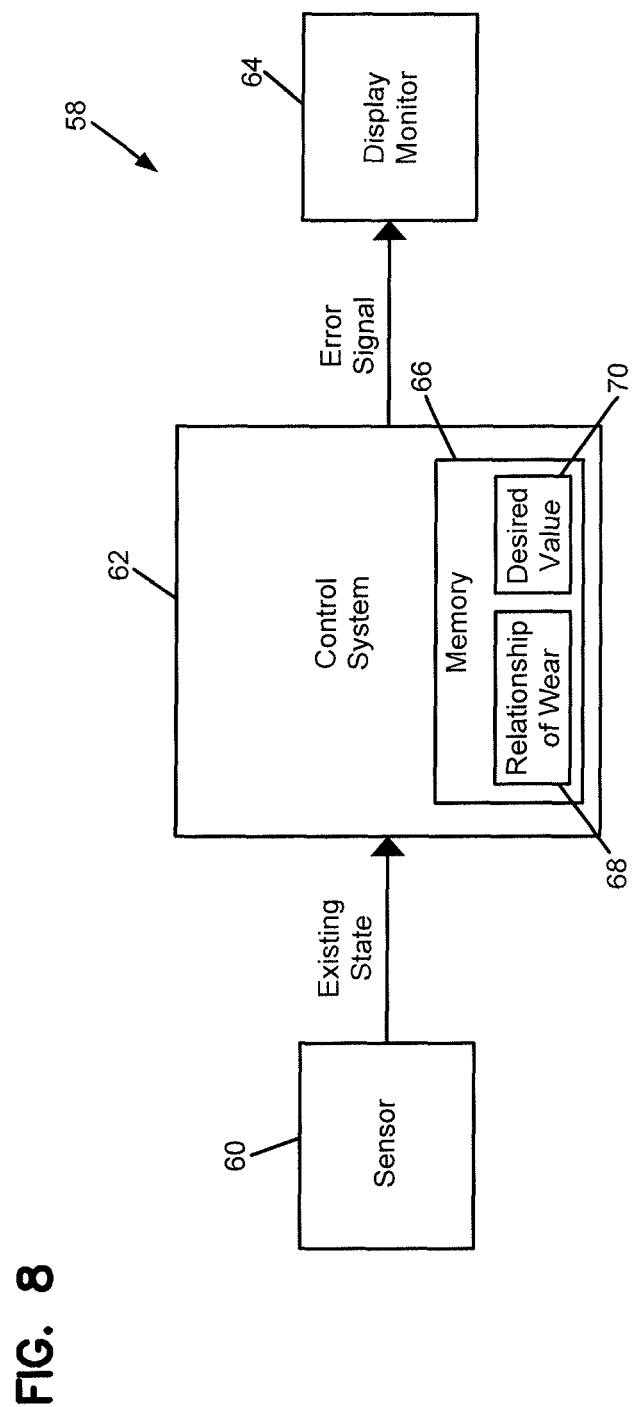
FIG. 8 illustrates an example of a sensing system in accordance with the principles of the present disclosure.

Referring to FIG. 8, an example of a sensing system 58 is illustrated. The sensing system 58 can be used to determine the wear state of the reducing elements 40. The sensing system 58 can include a sensor 60 or an array of sensors 60, a control system 62, and the display monitor 64. In one example, the sensor 60 is configured to sense an unworn state of the reducing elements 40 and relay information indicative of the unworn state to the control system 62. The sensor 60 can be configured to detect the wear state of the reducing elements 40 during operation. As the reducing elements 40 dig into the material under the excavation drum 36, the reducing elements 40 become worn. The sensor 60 may, for example, sense a change in the distance of the reducing elements 40 protruding from the mounting structures. In other examples, the sensor 60 may sense a change in the distance of the reducing elements 40 protruding from any location on the excavation drum 36. In one example, the sensor 60 may sense a distance from any reference point either on the excavation drum 36 or offset from the excavation drum 36. It is, however, to be understood that the sensor 60 could sense a parameter other than distance and still be within the scope of the present system, so long as the parameter can be used to detect the wear level of a given reducing element 40. For example, the sensor 60 could be a high-speed camera, infrared sensor, or magnetic field sensor, which could be used to monitor directly the contour of a given reducing element 40.

The control system 62 can include a memory 66 that stores a predetermined relationship of wear 68 and a desired value 70. Upon a change of the predetermined relationship of wear 68 that is greater than the desired value 70, the control system 62 can be configured to produce an error/warning signal. The error signal can be relayed to the display monitor 64, indicating the wear status of the reducing elements 40. The sensing system 58 can be used in autonomous situations where the operator is monitoring multiple machines working in tandem. In such examples, the control system 62 for the autonomous machine may also automatically stop operation of the autonomous machine once a given tooth goes beyond the desired value 70 for wearing. The display monitor 64 can be mounted on the machine, or the display monitor 64 can be remote (e.g. with remote operator).

In one example, the sensor 60 can include a laser scanner, a radar scanner, a charged coupled device or an infrared camera. In other examples, the sensor 60 can be used to measure the wear of the reducing elements 40 with a contactless measurement system or optical measurement. An example optical measurement system is disclosed at U.S. Pat. No. 8,386,196 B2, herein incorporated by reference in its entirety.

In certain examples, the sensing system 58 can include sensors 60 that generate alternating electromagnetic fields through which the reducing elements 40 pass as the reducing elements 40 are rotated about the axis of rotation 38 by the excavation drum 36. The reducing elements 40 can each have a metallic construction such that when the reducing elements 40 pass through the electromagnetic fields of the sensors 60, eddy currents form on the surface of the reducing elements 40. The amount of energy that is transferred by this phenomenon is directly dependent upon the surface area of the reducing element 40 passing through the field. The amount of energy transferred from the magnetic field can be detected and is represented by a decrease in electric current at the sensor 60. Since the amount of energy transferred is dependent upon the size of the object passing through the magnetic field, the amount of current reduction sensed as a reducing element 40 passes through the magnetic field is representative of the size of the reducing element 40.

As the reducing element 40 wears during use, the surface area of the reducing elements 40 passing through the magnetic field of its corresponding sensor 60 is reduced such that less energy is transferred to the reducing elements 40 as the reducing elements 40 pass through the magnetic field. Since less energy is transferred to the reducing elements 40, a smaller reduction in current is sensed. Thus, by monitoring the magnitude of current reduction sensed as the reducing elements 40 pass through the magnetic field, it is possible to monitor the wear state of the reducing elements 40 corresponding to the sensor 60. Example methods for monitoring wear are disclosed at PCT Patent Application No. PCT/US2013/074672, herein incorporated by reference in its entirety.

In certain examples, a remote display can be used to make data available to operators in a remote vehicle. Communications to the remote display can bring attention of a wear state change to the remote operator. In one example, the operator can select one of the reducing elements 40 by pressing a button, clicking on/trouching a screen icon, etc., specifically for that reducing element 40 that needs to be changed, and the control system 62 will automatically index the excavation drum 36. In particular, the excavation drum 36 will be indexed so that the selected reducing element 40 is at the change-out position P suitable for accessing and replacing the reducing element 40. The control system 62 can automatically rotate the excavation drum 36 to align with the specific row including the reducing element 40 to be changed, while skipping all the other rows. The control system 62 can be provided with an algorithm or other control logic that automatically moves a selected reducing element 40 to the change-out position P upon request by the operator. In other examples, the algorithm can automatically position reducing elements 40 in need of change at the change-out position P.

In other examples, the operator can remotely control the position of the excavation drum 36 using the display monitor 64 to provide feedback regarding the rotational position of the excavation drum 36. In one example, the sensing system 58 of the autonomous machine can notify a remote operator of an upcoming need to switch out one or more reducing elements 40. A wireless communication of the wear status of each machine can be sent to the operator and viewed on the display monitor 64. Through wireless communication, a remote operator can rotate the excavation drum 36 to the change-out position P for replacing the reducing element 40. In other examples, the sensing system 58 can provide an auto-shutdown when a reducing element 40 is missing and/or has gone beyond a critical wear level.

If the reducing element 40 is good, the sensing system 58 allows for the operator to recalibrate the reducing element 40 based on its calibrated reading and its last reading using the location of the reducing element 40 on the excavation drum 36. In certain examples, the sensing system 58 can include a reducing element change assist feature. The change assist feature can be configured to notify the operator of the location of the bad reducing element 40 such that the operator can change the reducing element 40 more ergonomically and/or more easily. In other examples, an automatic reducing element change system can be used to change out the reducing element 40.

In certain examples, the display monitor 64 of the sensing system 58 can communicate with a remote third party (e.g., supply source, main office, warehouse, etc.) simultaneously to notify the party when a reducing element 40 is approaching a need for replacement. In such situations, the remote operator can coordinate replacing the reducing element 40 with the delivery of the replacement part. This system can help to save time on part orders, as the remote monitoring parts can, for example, be pre-ordered as the remote third party is made aware of the wear status of the reducing elements 40. It will be appreciated that the wear sensing of the reducing elements 40 can be automated. Furthermore, the remote third party can be provided with a report that summarizes which reducing elements 40 were and/or need to be replaced and how many. This can allow for the remote third party to maintain an accurate inventory of supplies for replacement parts and better monitor how often the reducing elements 40 are replaced, as well as plan for incoming orders.

Figure 9:
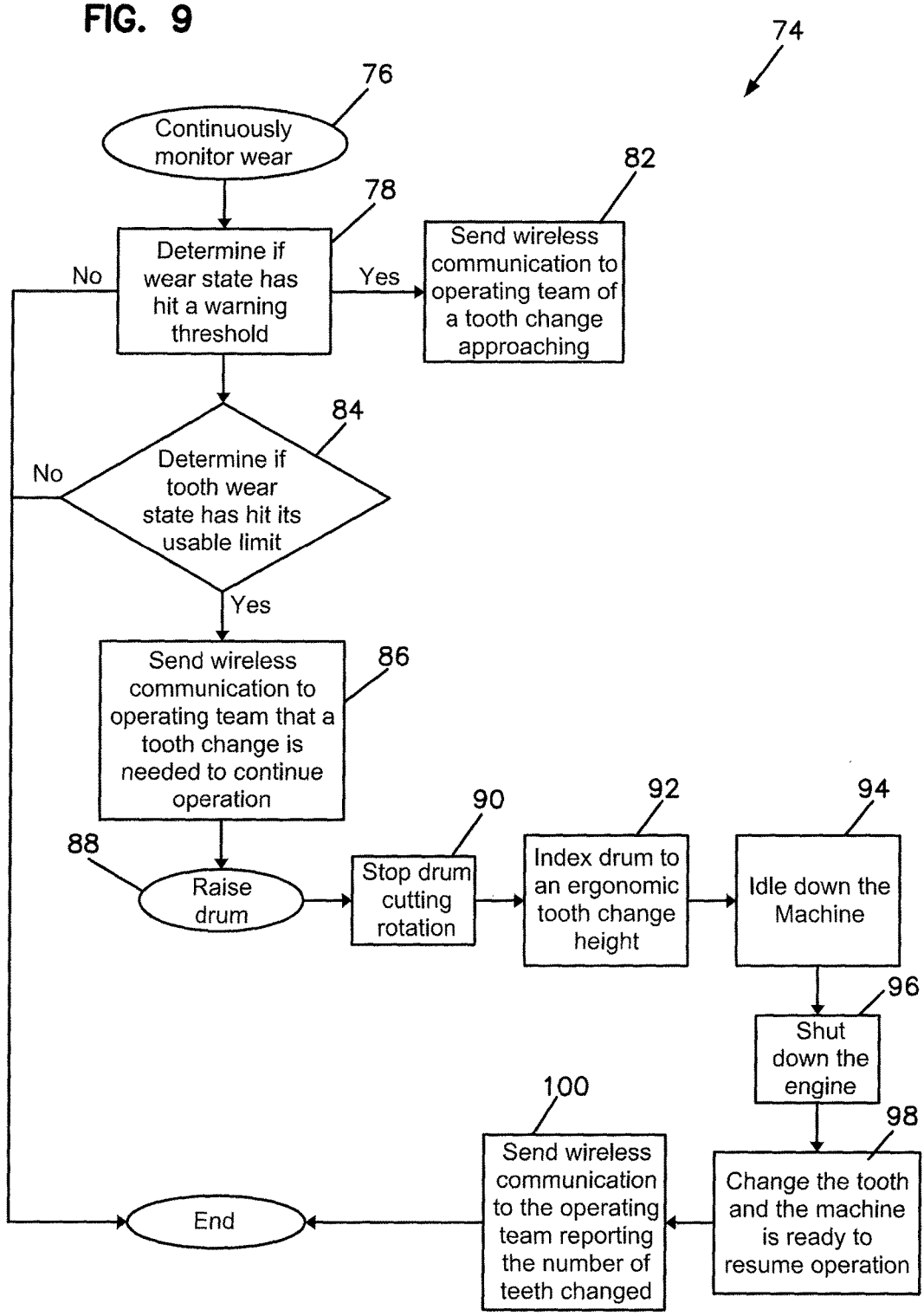
FIG. 9 is a flow chart depicting an example method for detecting wear of the reducing elements in accordance with the principles of the present disclosure.

Referring to FIG. 9, a flow chart depicting an example method 74 for controlling an autonomous system is displayed. The method includes detecting wear of the reducing element 40. In particular, the method 74 describes an automatic control protocol for replacing worn reducing elements 40. In block 76, the reducing elements 40 are continuously monitored for detectable wear. As described above, a remote operator can monitor the wear of the reducing elements 40 using the display monitor 64, as described above.

In block 78, a determination is made as to whether the wear state of the reducing elements 40 has reached a warning threshold. In other words, it is determined whether a change between a desired predetermined relationship of wear stored in the control system memory 66 and the existing predetermined relationship is greater than the desired value 70. If the warning threshold has not been reached, the sequence ends. If there has been a change that meets the warning threshold, control passes to block 82. Of course, other pre-warning thresholds could be defined. For example, in the green-yellow-red scheme, a pre-warning threshold could be used to change the indicator color from green to yellow, thus indicating a level of wear that could be used, e.g., to trigger ordering of a replacement reducing element 40 and/or to alert the operator to the approaching end-of-lifecycle for the given reducing element 40.

In block 82, a wireless communication can be sent to an operating team to alert them of a reducing element 40 (e.g., tooth, chisel, etc.) change approaching. In one example, the operating team can include a primary operator responsible for changing the reducing elements 40. The primary operator may also be in charge of starting and stopping the different autonomous processes. The primary operator may also oversee and check the error or warnings messages. In other examples, the operating team may include a secondary operator that has the same general roles as the primary operator. The secondary operator can provide additional man power to change the reducing elements 40. In certain examples, the operating team may include supervisory staffs responsible for making the autonomous machine and operators run successfully and may also include management and performance tracking staff.

In block 84, a determination is made as to whether the wear state of the reducing elements 40 has reached its usable limit. If the change in the wear state of the reducing elements 40 is within a predetermined value, the sequence ends. If the change in the wear state of the reducing elements 40 is greater than a desired predetermined value of use, the sequences passes to block 86. The determination of wear in block 84 can function as a safety mechanism to protect the surface excavation machine 20.

In block 86, a wireless communication is configured to be sent to the operating team to alert the operating team that a reducing element 40 replacement is needed in order to continue operation. Such an alert can be an indication to the autonomous machine to begin the changeover process. The first step of the changeover process is described in block 88. Block 88 of the sequence raises the excavation drum 36. In block 90 of the method, the excavation drum 36 rotation is stopped in preparation of the replacement of the reducing elements 40.

Once the excavation drum 36 is stopped, block 92 of the method allows for the excavation drum 36 to be indexed to an ergonomic position. The excavation drum 36 can be positioned such that the height and location of the reducing element 40 being replaced is easily accessible by the operator or an automatic tooth changing system.

In block 92, the method provides for the rotational position of the excavation drum 36 to be tracked along with the position of each reducing element 40. When a reducing element 40 is worn beyond its usable limit, the excavation drum 36 can be rotated such that the reducing element 40 to be replaced is at an ergonomic change position (i.e., the change-out position P) for easy reach and replacement. Because the sensing system 58 is configured to identify the reducing element 40 needing replacing, the specific position or location of the reducing elements 40 can be easily located to make the replacement. Thus the excavation drum 36 can automatically stop at the reducing element 40 to be changed. It is, however, to be understood that the steps of block 90 and block 92 could be reversed, with the excavation drum 36 being slowed down and indexed to a change-out position P and then stopped upon reaching such a position.

In block 94 of the method, the autonomous machine is idled down. The autonomous machine is maintained in a low idle for a cool down period. The sequence then passes to block 96 to shut down the engine.

In block 98, the method provides for the replacement of the reducing element 40 while the excavation drum 36 is held/stopped at the ergonomic change position (i.e., the change-out position P). During this sequence of replacement, a remote control (not shown) can be used to index through the remainder of the reducing elements 40. For example, after each replacement the remote control can be used to advance to the next reducing element 40 in need of change. After all the identified reducing elements 40 have been changed, the autonomous machine can resume operation and move forward.

In block 100, the method allows for a wireless communication to be sent to the operating team informing them of the number of reducing elements 40 that were replaced. In one example, data can be generated to track reducing element 40 changes per tool holder basis. In certain examples, replacement of reducing elements 40 can be tracked on a per tool holder basis. In such instances, the replacement data can be used to monitor service for each tool holder. In other examples, data can be collected in regard to wear comparisons between cutter design modifications. In certain examples, the amount of data generated can help determine the duration of operation between each wear replacement and the severity of the wear for each reducing element 40.

Wireless communications of reducing elements 40 (see FIG. 2) wear status and warnings of the same can be sent through multiple means. In one example, the wireless communication can include a wireless remote control radio frequency. The remote may include a LCD display to provide clear communication of the wear status of the reducing elements 40 via color codes, number codes, letter codes, etc. In certain examples, the wireless communication may be a telematics type communication. The telematics technique can be used to manage and track performance of the reducing elements 40. The telematics can utilize Wi-Fi, satellite, direct radio communication, and/or cellular communication to get data out to a server where the data can then be processed and further accessed through the internet. This technique will maintain records of reducing element wear and allow for trend monitoring. It is to be understood that a hard-wired communication could be possible in the present system if, for example, the sensor and display are both local (i.e., on the excavator).

Figure 10:
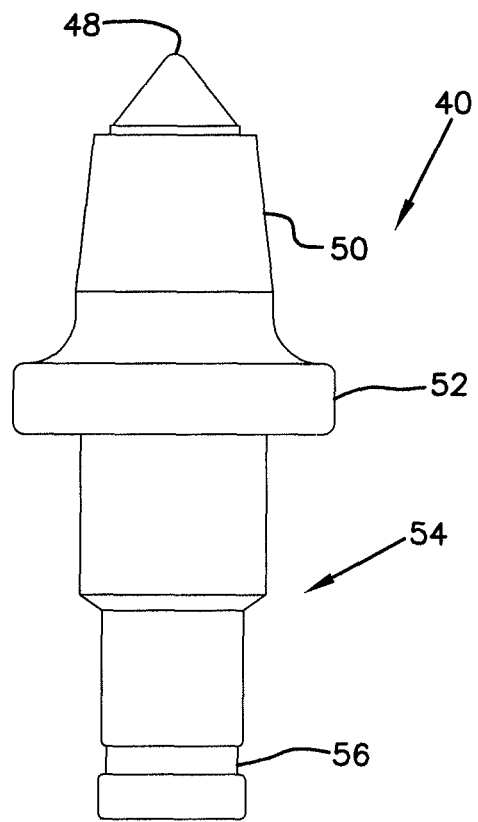
FIG. 10 shows a reducing element that can be used with the machine of FIG. 1.

Referring to FIG. 10, an example of the reducing element 40 is shown. The reducing element 40 is depicted as a tooth having a leading tip 48 supported on a base 50. In other embodiments, the reducing elements 40 may include a cutter, a pick, a chisel, a blade, or other type of cutting, grinding, or comminuting device. In certain examples, the leading tip 48 can be harder than the base 50. For example, leading tip 48 can be a solid, carbide insert while the base 50 can be hardened steel. In certain examples, the reducing elements 40 are removably mounted to the excavation drum 36. For example, the reducing elements 40 can be fastened within mounting structures such as pockets (not shown) integrated with the excavation drum 36.

In certain examples, the reducing element 40 further includes a shoulder 52, a shaft 54, and a circumferential groove 56. The shoulder 52 extends radially outwardly from the base 50 and has a cross-dimension larger than a maximum cross-dimension of the base 50. The shaft 54 extends axially from the shoulder 52 of the reducing element 40 and has a narrower cross-dimension than that of the shoulder 52. The shaft 54 of the reducing element 40 may further include an inwardly tapered section along the shaft 54. The reducing elements 40 are constructed to fit into mounting structures that are integrated with or otherwise coupled to drums or chains used to carry the reducing element 40 during material reducing applications. The reducing elements 40 are designed to be readily replaceable upon detection of wear.

From the forgoing detailed description, it will be evident that modifications and variations can be made without departing from the spirit and scope of the disclosure.

What is claimed is:

1. A method for controlling an autonomous system, the method comprising:
sensing a wear state of reducing elements on a drum of an excavation machine;
sending a wireless signal of the wear state to a remote party; and
displaying the wear state of the reducing elements on a display monitor, wherein the display monitor is constructed to display a continuous scroll of the reducing elements, wherein a rotational position of the reducing elements relative to a reference location is displayed, and wherein the reference location is a change-out position.

2. The method of claim 1, wherein the remote party is one of an operator and a third party.

3. The method of claim 2, wherein the remote party is the third party, and the third party includes a supply source, a main office, or a warehouse.

4. The method of claim 1, wherein the reducing elements are displayed all at once in real time on the display monitor.

5. The method of claim 1, wherein the method further comprises automatically indexing the drum to the change-out position using an algorithm.

6. The method of claim 1, wherein the method includes the steps of monitoring multiple machines and displaying remotely on the display monitor the wear state of the reducing elements on each of the multiple machines.

7. An automatic control method for monitoring and diagnosing reducing elements on an excavation drum of an excavation machine, a sensing system being integrated with a control system for monitoring and diagnosing the reducing elements, the method comprising:
monitoring a wear state of the reducing elements during operation;
sensing a change in the wear state of the reducing elements;
sending a communication of the wear state of the reducing elements to a display structure integrated with the control system;
upon detection of the change in the wear state beyond a usable limit, alerting an operator to replace the reducing elements;
shutting down operation of the excavation machine based on the wear state of the reducing elements;
raising the excavation drum;
indexing the excavation drum to an ergonomic position in preparation of replacing the reducing elements; and
replacing the reducing elements while the drum is held at the ergonomic position for replacing the reducing elements.

8. The method of claim 7, wherein the wear status is in the form of a code, the code is selected from the group consisting of: color codes; number codes; and letter codes.

9. The method of claim 7, wherein the display structure visually depicts all the reducing elements in a scrolling matrix.

10. The method of claim 7, further facilitating controls for use in autonomous situations where the operator is simultaneously monitoring multiple machines.

11. The method of claim 7, further comprising sending a wireless communication to a third party upon detection of the wear state of the reducing elements beyond the usable limit.

12. The method of claim 7, wherein the display structure is provided so that the operator utilizes the display structure to manually and ergonomically align the reducing elements on the excavation drum to a change-out position.

13. The method of claim 7, wherein the control system includes an algorithm for automatically turning the excavation drum to a desired change-out position for replacement of the reducing elements.

14. The method of claim 7, wherein the respective wear states of the reducing elements are displayed all at once in real time on the display structure.

15. A display structure, the display structure being integrated with a sensing system for monitoring and diagnosing reducing elements on an excavation machine, the sensing system including a control system in communication with a memory and the display structure, the display structure comprising:
a display including a display screen, the display being adapted to show a wear status of all of the reducing elements at once;
wherein the display is configured to show a rolling scroll of the reducing elements such that a rotational position of the reducing elements relative to a reference location is displayed; and
wherein the memory is configured to store information relating to the wear status of the reducing elements.

16. The display structure of claim 15, wherein rotational positions of all the reducing elements are shown in real time.

17. The display structure of claim 15, wherein the display is configured to display the wear status of reducing elements of multiple remote machines when the multiple remote machines are being monitored.

* * * * *